United States Patent [19]

Harrington et al.

[11] 4,076,519
[45] Feb. 28, 1978

[54] N-SUBSTITUTED PERFLUOROALKANESULFONAMIDES AS HERBICIDES

[75] Inventors: Joseph Kenneth Harrington, Edina; Donald C. Kvam, North Oaks; Arthur Mendel, Vadnais Heights; Jerry E. Robertson, North Oaks, all of Minn.

[73] Assignee: Minnesota Mining and Manufacturing Company, St. Paul, Minn.

[21] Appl. No.: 618,376

[22] Filed: Oct. 1, 1975

Related U.S. Application Data

[60] Division of Ser. No. 352,596, Apr. 19, 1973, Pat. No. 3,920,444, which is a continuation-in-part of Ser. No. 100,404, Dec. 21, 1970, abandoned, which is a division of Ser. No. 832,829, Jun. 12, 1969, Pat. No. 3,639,474, which is a continuation-in-part of Ser. No. 588,338, Oct. 21, 1966, abandoned.

[51] Int. Cl.² .............................................. A01N 9/16
[52] U.S. Cl. ......................................... 71/103; 71/76; 71/78
[58] Field of Search ......................................... 71/103

[56] References Cited

U.S. PATENT DOCUMENTS

| 3,629,332 | 12/1971 | Harrington et al. | 71/103 |
| 3,637,845 | 1/1972 | Moore et al. | 71/103 |
| 3,734,710 | 5/1973 | Lukaszezyk et al. | 71/103 |
| 3,793,372 | 2/1974 | Gerster | 71/103 |

Primary Examiner—Lewis Gotts
Assistant Examiner—Catherine L. Mills
Attorney, Agent, or Firm—Cruzan Alexander; Donald M. Sell; Donald C. Gipple

[57] ABSTRACT

N-Substituted perfluoroalkanesulfonamides of the formula:

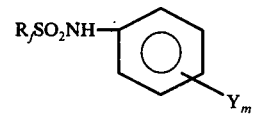

wherein $R_f$ is perfluoroalkyl group containing one to four carbon atoms, each Y is a non-cyclic group which can contain only carbon, hydrogen, oxygen, sulfur, nitrogen and halogen and $m$ is 1–5, provided that all of the Y groups together contain not more than about twenty carbon atoms and that at least one of the Y groups contains a heteroatom selected from oxygen, sulfur, nitrogen and halogen. Also included are salts of these compounds, compositions containing the compounds of the present invention and processes for their preparation and use. The compounds are active as herbicides and plant growth modifiers.

48 Claims, No Drawings

N-SUBSTITUTED PERFLUOROALKANESULFONAMIDES AS HERBICIDES

This application is a division of copending application Ser. No. 352,596 filed Apr. 19, 1973 (now issued as U.S. Pat. No. 3,920,444), Ser. No. 352,596 being a continuation-in-part of copending application Ser. No. 100,404 filed Dec. 21, 1970, (now abandoned) Ser. No. 100,404 being a division of application Ser. No. 832,829 filed June 12, 1969, (now issued as U.S. Pat. No. 3,639,474) Ser. No. 832,829 being, in turn, a continuation-in-part of application Ser. No. 588,338 filed Oct. 21, 1966 now abandoned.

The invention relates to N-substituted perfluoroalkanesulfonamides which have activity as herbicides and plant growth modifiers.

Perfluoroalkanesulfonamides have been disclosed broadly heretofore (see, for example, U.S. Pat. Nos. 2,732,398 and 3,321,445) but there has been no indication of any herbicidal activity of such compounds.

In the N-substituted perfluoroalkanesulfonamides of the present invention, the amide nitrogen substituent is a phenylene ring having from one to five substituent groups containing only carbon, hydrogen, oxygen, sulfur, nitrogen and halogen and at least one of which must contain oxygen, sulfur, nitrogen or halogen. The invention includes salts of the compounds, processes for their preparation, compositions containing them and methods for their use as herbicides, and plant growth modifiers.

It is an object of the invention to provide compounds which modify the growth of plants, i.e. compounds which prevent, alter, destroy or otherwise affect the growth of plants.

It is a further object of the invention to provide a method for controlling unwanted plants.

It is another object of the invention to provide herbicidal compositions containing one or more perfluoroalkanesulfonamides as active ingredients therein.

It is another object of the invention to provide compounds which are active anti-inflammatory agents.

It is a particular object of the invention to provide a method for the control of tobacco suckers which comprises contacting tobacco plants with an effective amount of a perfluoroalkanesulfonamide.

Still other objects of the invention will be made apparent by the following specification.

DETAILED DESCRIPTION

According to the present invention there is provided a class of compounds consisting of perfluoroalkanesulfonamides having the general formula:

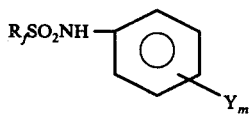

I and metal, ammonium and organic amine salts thereof wherein $R_f$ is a perfluoroalkyl group containing one to four carbon atoms, each Y is a non-cyclic group which can contain only carbon, hydrogen, oxygen, sulfur, nitrogen and halogen and m is 1-5, provided that all of the Y groups together contain not more than about twenty carbon atoms and that at least one of the Y groups contains a heteroatom selected from oxygen, sulfur, nitrogen and halogen. In the metal, ammonium and organic amine salts, the amide hydrogen of the formula is replaced by a suitable cation.

The salts of the invention are prepared by treating the acid form (shown in the foregoing formula I) with a stoichiometrically equivalent amount of an appropriate base under mild conditions. Among the metal salts of the invention are alkali metal (e.g. lithium, sodium and potassium), alkaline earth metal (e.g. barium, calcium and magnesium) and heavy metal (e.g. zinc and iron) salts as well as other metal salts such as aluminum. Appropriate bases for use in preparing the metal salts include metal oxides, hydroxides, carbonates, bicarbonates and alkoxides. Some salts are also prepared by transmetallation reactions. The organic amine salts include the salts of aliphatic (e.g. alkyl), aromatic and heterocyclic amines, as well as those having a mixture of these types of structures. The amines useful in preparing the salts of the invention can be primary, secondary or tertiary and preferably contain not more than 20 carbon atoms. Such amines include, for example, morpholine, methyl cyclohexylamine, glucosamine, amines derived from fatty acids, dialkanolamines such as diethanolamine, etc. These and the ammonium salts can be prepared by reacting the acid form with the appropriate organic base or ammonium hydroxide. The salts of the invention are frequently formed by reacting the precursors in aqueous solution. This solution can be evaporated to obtain the salt of the compound as a dry powder. In some cases, it may be more convenient to use a non-aqueous solvent such as alcohols, acetone, etc. Since many of the salts are water soluble, they are often used in the form of aqueous solutions.

Due to the acidity of the hydrogen of the amido group of formula I, the compounds of the invention are catalysts for certain acid-catalyzed polymerizations, e.g. polymerization of epoxides. Many of the compounds of the invention are anti-microbial agents, according to standard test procedures. Also, some of the compounds (including those wherein Y is halogen, nitro, alkoxy and alkanoyl) have been found to possess anti-inflammatory activity in standard screening test procedures using experimental animals.

The heteroatoms in the Y group or groups can be present in substituents including alkyl, alkanoylamido, halo, haloalkyl, nitro, alkoxy, N-alkylcarbamyloxy, alkanoyl semicarbazone, alkylsulfonyl, alkylsulfinyl, alkylthio, amino, alkylamino, alkylsulfamido, hydroxy, hydroxyalkyl, carboalkoxy, sulfamoyl, dialkylamino, carbamyl, alkanoyl, haloalkanoyl, haloalkanoylamido, cyano, aldehydo, alkanoyl oxime, carbamoylmethylamino, haloalkylthio, haloalkylsulfinyl, haloalkylsulfonyl, carboxyalkyl, haloalkoxy, carboalkoxymethylamino, mercapto, alkylsulfonato, haloalkylsulfonato, carboalkoxyamino, alkoxyalkylthio and sulfamoylamino. Thus, as noted previously, Y is noncyclic, i.e. contains no cycles of any kind (either aliphatic or aromatic). Preferably, no single Y group contains more than 6 carbon atoms. Most preferred are compounds in which no single Y group contains more than 4 carbon atoms.

Compounds of the invention may be substituted by lower alkyl groups in addition to heteroatom-containing substituents, i.e. on the aromatic ring.

Preferably, $R_f$ in the compounds of the invention is trifluoromethyl. Price is an important consideration in herbicides and such compounds offer more economical utilization of fluorine together with high activity. Preferably also, not more than two of the Y groups are other than halogen.

Another preferred group consists of those compounds in which the Y group together contain not more than about six carbon atoms. Other preferred groups of the compounds are those in which all of the Y groups are halogen and those in which at least one of the Y groups is alkylthio, alkylsulfinyl, alkylsulfonyl, haloalkyl, sulfamoyl, alkanoylamido, sulfamoylamino, alkoxyalkylthio and carbamyl. Particularly preferred are compounds in which all of the Y groups are selected from halo, alkyl, alkylthio, alkylsulfinyl, alkylsulfonyl, haloalkyl, sulfamoyl, alkanoylamido, sulfamoylamino, alkoxyalkylthio and carbamyl. Finally those compounds in which $m$ is 1-3, particularly in which $m$ is 1, are preferred.

In order to control unwanted plants, the compounds of the invention can be used alone as herbicides, for example, as dusts or granules of the compounds, or preferably they may be applied in formulations containing the active ingredients in a horticulturally acceptable extending medium. The formulations are comprised of one or more active ingredients and one or more herbicidal adjuvants and/or carriers. Specific formulations are useful to facilitate the application of the compounds and to achieve specific biological objectives such as controlling the availability of the herbicide, improving adherence to plants, and the like, as is well known to those skilled in the art.

The compounds of the invention may be formulated as wettable powders, emulsifiable concentrates, aqueous or nonaqueous solutions and/or suspensions, granules, dusts and the like. Said compounds as such can be finely divided and dispersed or suspended in any of the usual aqueous media, or if appropriate salts are used, a solution may be made. Spreading agents, wetting agents, sticking agents or other adjuvants can be added as desired.

When emulsifiable concentrates are prepared the active ingredient can be present in concentration of about 5% to 60% or more, depending upon its solubility, but it has been found that the compounds of this invention are preferably used in a concentration of 20 to 30%. The units of concentration are weight per unit weight. When the active ingredients are not in salt form, they are soluble in common organic horticultural solvents such as benzene, toluene, xylene, dichloromethane, chloroform, hexane and heptane or less highly refined aromatic or aliphatic hydrocarbons and mixtures thereof. Examples of these are coal tar fractions, straight run petroleum distillates, thermolytically or catalytically cracked hydrocarbon oil, gas oil, light lubricating oil fractions, kerosene, mineral seal oil, and the like. In appropriate cases, oxygenated solvents such as ketones may be used in or as the carriers. These concentrates can be dispersed in water to permit the use of an aqueous spray. Admixture with a small amount of an organic surface active agent capable of lowering the surface tension of water is preferred, so as to produce more or less stable emulsions.

Examples of surface active agents variously known as dispersing agents, wetting agents or emulsifying agents comprise soft or hard soaps, morpholine or dimethylamine oleate, sulfonated fish, castor and petroleum oils, sodium salts of lignin sulfonic acid, alkylated aromatic sodium sulfonates, such as decylbenzene sodium sulfonate, dodecylbenzene sodium sulfonate, butyl or other amine salts of decyl or dodecylbenzene sulfonic acid, sodium lauryl sulfate, disodium monolauryl phosphate, ethylene oxide condensation products of alkyl phenols, as for example octyl phenol, ethylene oxide condensation products of tall oil and ethylene oxide condensation products of higher alcohols or higher mercaptans. Mixtures of two or more surface active agents are also feasible. Generally, the surface active agent will comprise only a small proportion of the composition, say 0.1-15% by weight of the toxicant.

The formulation of dry compositions for application as granules, dusts or for further dilution with liquid carriers is readily accomplished by mixing the toxicant with a solid carrier. Such solid carriers will be of various sizes from dust to granules. The techniques for such formulations are well known to the art. Suitable carriers include charcoal, talc, clay, pyrophyllite, silicas, fuller's earth, lime, diatomaceous earth, flours such as walnut shell, wheat, soya bean, cottonseed and wood flours, magnesium and calcium carbonate, calcium phosphate and the like. Powders may be granulated by the use of suitable binders such as cellulose derivatives, for example ethyl or carboxymethyl, corn syrup, and the like. The compounds or the above formulations are applied by spraying, spreading, dusting or the like. The rate of application will of course vary, but the more active compounds of the invention exhibit satisfactory control of broadleaf and grass weeds at the application rate of about 1 to 15 pounds per acre. It is of course to be expected that local conditions, for example temperature, humidity, moisture content of the soil, nature of the soil, and the like, may require greater or smaller amounts. Effective resolution of these factors is within the skill of those versed in the herbicidal art. Likewise it is apparent that not all of the compounds included within the scope of the invention have equal activity.

The herbicidal compositions may contain one or more of the herbicidal compounds set out hereinbefore as the sole active species, or they may contain in addition thereto other biologically active substances. Thus insecticides and fungicides may be incorporated in the compositions. Further, if desired, the herbicidal compositions may contain fertilizers, trace metals or the like and when applied directly to the soil may additionally contain nematicides, soil conditioners, plant growth regulators and/or herbicides of similar or different properties.

Presently especially preferred herbicidal compounds of this invention are 2,4-dichlorotrifluoromethanesulfonanilide (Example 3), 2,4-difluorotrifluoromethanesulfonanilide (Example 26), 3-methylthiotrifluoromethanesulfonanilide (Example 42), 2-fluoro-4-chlorotrifluoromethanesulfonanilide (Example 84), 2-chloro-4-fluorotrifluoromethanesulfonanilide (Example 83), 4-chlorotrifluoromethanesulfonanilide (Example 11), and 4-trifluoromethyltrifluoromethanesulfonanilide (Example 19).

The compounds of this invention are broadly active as herbicides. However, many of the compounds of the invention also show various types of plant growth modifying activity. Plant growth modification as defined herein consists of all deviations from natural development, for example, defoliation, stimulation, stunting, retardation, desiccation, tillering, dwarfing, regulation and the like. This plant growth modifying activity is generally observed as the compounds of the invention begin to interfere with certain processes within the plant. If these processes are essential, the plant will die if treated with a sufficient dose of the compound. However, the type of growth modifying activity observed varies among types of plants. It has been found that with certain compounds of the invention, herbicidal activity can be separated from certain other plant growth modifying activities by controlling the rate of application. Of particular interest is the ability of some compounds of the invention to give tobacco sucker control. This phenomenon is known to the art to be desirable and useful, since the control of tobacco suckers increases the useful yield of the tobacco plant. 5-Acetamido-2-methyltrifluoromethanesulfonanilide (Example 12) is particularly active in the control of tobacco suckers. These growth regulant compounds have also been found to retard the growth of some plants without significant distortion of the normal foliar shape. This activity has been of particular interest when it occurs on grass species. This desirable and useful activity is present in a particularly high degree in 5-acetamido-2-methyltrifluoromethanesulfonanilide (Example 12) and 5-acetamido-2-chlorotrifluoromethanesulfonanilide (Example 164).

Broadly speaking, the compounds of this invention are readily prepared by one or all of the following methods, each of which is illustrated by an equation.

Method A

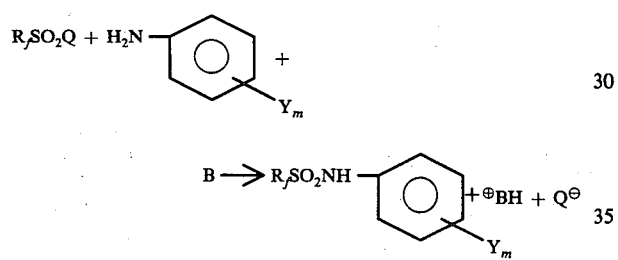

where Q is a halogen or perfluoroalkanesulfonate residue, B is an organic or inorganic base and $R_f$, Y and $m$ are as defined above.

A solution of the appropriate primary arylamine and an equimolar quantity of a suitable acid acceptor (such as triethylamine, dimethylaniline, pyridine and the like) in an inert organic solvent is ordinarily used. However, an acid acceptor is not always necessary, and an excess of the primary arylamine may also serve as acid acceptor. Among the suitable solvents are 1,2-dimethoxyethane, benzene, chloroform, dichloromethane, dimethylacetamide, dimethylformamide and the like. Alternatively an excess of the primary arylamine or the acid acceptor may serve as a solvent, or the reaction may be carried out in the absence of solvent. Generally, an equimolar quantity of the appropriate perfluoroalkane sulfonic anhydride or halide is added to the solution. The addition is advantageously carried out at $-15°$ C. to $50°$ C., and for some reactants higher or lower temperatures may be preferable. In cases where the amine is of lower reactivity, it is advantageous to allow the reaction mixture to remain at reflux temperature for a few hours following addition.

The reaction of Method A may also be carried out in a high pressure reactor. This technique is particularly preferred when perfluoroalkanesulfonyl fluorides are used as reactants. These reactions are usually carried out at temperature ranges of $0°$ to $150°$ C., but these temperature ranges may be raised or lowered, depending upon the reactants used. Such reactions are most frequently carried out without solvent, or with dimethylformamide or excess triethylamine as solvent, but other advantageous variations are possible.

It will be appreciated that the scope of this invention encompasses starting materials of a wide range of physical and chemical properties, and the synthetic methods A, B and C discussed herein are described in general and preferred language. However, a great variation in the use of these synthetic techniques is possible, and this invention is broadly inclusive of such variations.

After completion of the reaction, the product is isolated by conventional methods. For example, the reaction mixture can be extracted with excess aqueous sodium hydroxide. The aqueous extract is then washed with organic solvents and treated with charcoal to remove impurities. Subsequent acidification of the aqueous extract with mineral acid then affords the product as an oil or solid which is distilled, sublimed, chromatographed or recrystallized as required to give pure product. When water-soluble solvents are used, the reaction mixture can be poured directly into aqueous mineral acids. The product is then isolated by conventional extraction techniques and purified as above.

Method B

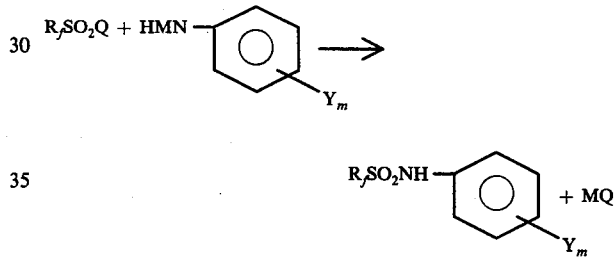

where M is an alkali metal and Q, $R_f$, Y and $m$ are as defined above.

An alkali metal salt of the appropriate amine is prepared by any of several conventional methods such as by reaction with sodium naphthalene, a metal hydride such as sodium hydride, alkoxides such as potassium t-butoxide in protic or aprotic solvents, or by reaction with an alkali metal such as sodium or potassium directly in an appropriate solvent.

The resulting salt is then treated with a perfluoroalkanesulfonyl alkylating agent such as trifluoromethanesulfonyl fluoride or chloride or trifluoromethanesulfonic anhydride, either at atmospheric pressure in open apparatus or under pressure in a pressure vessel. The reaction takes place at $0°$ to $150°$ C., depending on the reactivity of the amine and the sulfonyl halide. On completion of the reaction, the product is obtained by conventional work-up techniques as described in Method A.

Method C

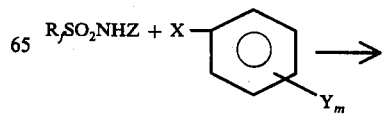

-continued

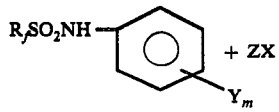

$R_f$, Y and m are as defined above, X is halogen and Z is an alkaline earth or alkali metal. The perfluoroalkanesulfonamide salt and an appropriate aryl halide are reacted, generally in a suitable solvent (such as dimethylsulfoxide, dimethylformamide, 1,2-dimethoxyethane, dimethylacetamide and the like). Heating or cooling, usually the former, may be advantageous to obtain a desirable rate of reaction.

After the completion of the reaction product is isolated by conventional methods. For example, when the reaction mixture is diluted with water the product may precipitate. Alternatively, the product may be extracted from the reaction mixture after dilution with water. Other recovery techniques are well known to those skilled in the art.

The reaction of Method C may also be carried in a high pressure reactor.

Method C is usually most valuable when the aryl halide is activated by suitable electron-withdrawing groups on the ring, as is well known to the art. Suitable aryl halides for use in Method C are well known to the art, as are salts of perfluoroalkanesulfonamides.

Suitable perfluorocarbonsulfonyl anhydrides and halides (e.g. chlorides and fluorides) for use in these procedures are known to the art (thus see U.S. Pat. No. 2,732,398). Similarly, the amines used in producing the compounds of this invention are described in the general chemical literature or are otherwise known to those skilled in the art. Among the suitable amines are haloanilines, halotoluidines, trifluoromethylanilines, acylanilines, nitroanilines, alkoxyanilines, hydroxy anilines, aminoanilines, acylamidoanilines, alkylthioanilines, alkylsulfinylanilines, alkylsulfonylanilines, aminobenzamides, aminobenzenesulfonamides, and the like. These known compounds contain both mixtures of different substituents and multiplicities of single or mixed substituents.

Methods A, B and C are generally applicable (preferably Method A) to the preparation of compounds of the invention. However, it is sometimes preferable, in order to increase yields and minimize purification problems, to utilize compounds of the invention in conventional, known procedures to prepare other compounds of the invention. Thus, for example, 4-nitrotrifluoromethanesulfonanilide may be reduced easily to 4-aminotrifluoromethanesulfonanilide, and 4-aminotrifluoromethanesulfonanilide may be acetylated readily to give 4-acetamidotrifluoromethanesulfonanilide. A number of such procedures are described briefly in the examples.

Following are detailed examples showing the preparation of compounds of the invention using Methods A, B and C, and a number of examples in table form showing the preparation of the compounds of invention. An example describing the evaluation of representative compounds of the invention as herbicides is also included.

The examples are given for the purpose of further illustrating the procedures of the present invention, but are not intended, in any way, to be limiting on the scope thereof. Thus while the great majority of the examples relate to perfluoromethanesulfonamides, other perfluorocarbon groups can be substituted in place thereof.

Also, to avoid unduly multiplying the examples which have been selected to illustrate the invention, the examples will relate for the most part to compounds in the acid form, that is having a hydrogen atom bonded to the amide nitrogen. It is, however, understood that the corresponding salts of the invention are also easily prepared and are likewise contemplated. Such salts, which have a cation bonded to the amide nitrogen, are also useful as herbicides, and in some cases as plant growth modifiers.

EXAMPLE 1

To a stirred mixture of 4-aminoacetophenone (67.6 g., 0.49 mole), triethylamine (60 g., 0.60 mole) and chloroform (400 ml) was added trifluoromethanesulfonic anhydride (155 g., 0.55 mole), dropwise, with cooling in an ice bath. On completion of the addition, the resulting mixture was extracted several times with 10 percent aqueous sodium hydroxide. The combined aqueous extracts were acidified with concentrated hydrochloric acid and a white solid precipitated. After isolation by filtration, the solid was washed with water and dried to give 4-acetyltrifluoromethanesulfonanilide. Recrystallization from ethanol-water afforded an analytical sample of 4-acetyltrifluoromethanesulfonanilide, m.p. 143°–145° C. uncorrected.

Analysis: Calculated for $C_9H_8F_3NO_3S$: C, 40.3; H, 3.0 Found: C, 40.4; H, 3.2

EXAMPLE 2

To a stirred mixture of 4-nitroaniline (13.8 g., 0.10 mole) and triethylamine (11.1 g., 0.11 mole) in dry 1,2-dimethoxyethane (200 ml.) at 0°–5° C. was added trifluoromethanesulfonic anhydride (18.3 ml., 0.11 mole) over 1.5 hours. The mixture was allowed to reach room temperature and was then stirred overnight. After pouring into 500 ml. of 10 percent aqueous hydrochloric acid, three chloroform extractions were executed. The combined organic layers were dried over sodium sulfate and concentrated to a residue which was distilled to yield 4-nitrotrifluoromethanesulfonanilide, b.p. 150°–151° C./0.05 mm.

Analysis: Calculated for $C_7H_5F_3O_4N_2S$: C, 31.1; H, 1.9 Found: C, 31.5; H, 1.8

EXAMPLE 3

To a stirred solution of 2,4-dichloroaniline (15.2 g., 0.10 mole) and triethylamine (11.1 g., 0.11 mole) in chloroform (200 ml.) at 0°–5° C. was added trifluoromethanesulfonic anhydride (18.2 m., ca. 0.11 mole) over 1.5 hours. Stirring was continued at 0°–5° C. for 0.5 hours, then at reflux temperature for one hour. The reaction mixture was cooled, poured into 2 liters of water and extracted three times with chloroform. The combined organic layers were dried over sodium sulfate and concentrated to a residue which was recrystallized from hot hexane to yield pure 2,4-dichlorotrifluoromethanesulfonanilide, m.p. 89.5°–90.5° C.

Analysis: Calculated for $C_7H_4Cl_2F_3NO_3S$: C, 28.6; H, 1.4 Found: C, 28.7; H, 1.5

EXAMPLE 4

Sodium naphthalene was prepared from naphthalene (12.8 g., 0.1 mole), sodium (2.3 g., 0.1 g atom) and tetrahydrofuran (200 ml.). Thereafter, 2,4,6-trichloroaniline (19.6 g., 0.1 mole) was added under nitrogen at ice bath temperature.

The resulting brown mixture was transferred (N₂) to a nitrogen-purged autoclave and charged with trifluoromethanesulfonyl fluoride (15.2 g., 0.1 mole). The product was heated at 50° C. for 20 hours. Tetrahydrofuran was removed and the black residue was taken up in dichloromethane. The organic mixture was filtered and extracted with cold, dilute potassium hydroxide. The separated aqueous layer was acidified with hydrochloric acid to give an oily solid. Trituration with cold petroleum ether followed by sublimation yielded glistening white crystals of 2,4,6-trichlorotrifluoromethanesulfonanilide, m.p. 106°–107.5° C.

Analysis: Calculated for $C_7H_3Cl_3F_3NO_2S$: C, 25.6; H, 0.9; N, 4.3 Found: C, 25.5; H, 1.1; N, 4.3

Unless otherwise specified, the compounds set out in the following table have been prepared using Method A from known starting materials. The melting points are uncorrected.

| Example No. | | M.P. ° C. |
|---|---|---|
| 5 | 2-fluorotrifluoromethanesulfonanilide | 65.5–67.5 |
| 6 | 2,3,4,5,6-pentafluorotrifluoromethanesulfonanilide | 68–69 |
| 7 | 4-fluorotrifluoromethanesulfonanilide | 60.5–62.5 |
| 8 | 3-fluorotrifluoromethanesulfonanilide | 38–40 |
| 9 | 2-chlorotrifluoromethanesulfonanilide | 75.5–76.5 |
| 10 | 3-chlorotrifluoromethanesulfonanilide | 76–77 |
| 11 | 4-chlorotrifluoromethanesulfonanilide | 50.5–51.5 |
| 12 | 5-acetamido-2-methyltrifluoromethanesulfonanilide (1) | 175–176.5 |
| 13 | 4-bromotrifluoromethanesulfonanilide | 56.5–58 |
| 14 | 2-bromotrifluoromethanesulfonanilide | 73.5–75.5 |
| 15 | 3-bromotrifluoromethanesulfonanilide | 79–80.5 |
| 16 | 3-iodotrifluoromethanesulfonanilide | 79.5–81.0 |
| 17 | 4-iodotrifluoromethanesulfonanilide | 73–75 |
| 18 | 3-trifluoromethyltrifluoromethanesulfonanilide | 32–34 |
| 19 | 4-trifluoromethyltrifluoromethanesulfonanilide | 73.5–75.0 |
| 20 | 3,4-dichlorotrifluoromethanesulfonanilide | (2) |
| 21 | 2,3-dichlorotrifluoromethanesulfonanilide | 83–87 |
| 22 | 2,5-dichlorotrifluoromethanesulfonanilide | 71–73 |
| 23 | 3,5-dichlorotrifluoromethanesulfonanilide | 76.5–79 |
| 24 | 2,4-dibromotrifluoromethanesulfonanilide | 106–107 |
| 25 | 2,3,5,6-tetrafluorotrifluoromethanesulfonanilide | 93–95 |
| 26 | 2,4-difluorotrifluoromethanesulfonanilide | 64.0–65.5 |
| 27 | 2-chloro-5-trifluoromethyltrifluoromethanesulfonanilide (3) | 51–54 |
| 28 | 4-amino-3,5-dichlorotrifluoromethanesulfonanilide | 120–121.5 |
| 29 | 2,4,5-trichlorotrifluoromethanesulfonanilide (4) | 106–107 |
| 30 | 2,5-dimethoxytrifluoromethanesulfonanilide | 63–65 |
| 31 | 3,4-diethoxytrifluoromethanesulfonanilide | 78.2–79.2 |
| 32 | 5-chloro-2,4-dimethoxytrifluoromethanesulfonanilide | 109.5–110 |
| 33 | 2-nitrotrifluoromethanesulfonanilide | 68.5–69 |
| 34 | 3-nitrotrifluoromethanesulfonanilide | 64–66 |
| 35 | 2,4-dinitrotrifluoromethanesulfonanilide (5) | 107–108 |
| 36 | 4-chloro-2-nitrotrifluoromethanesulfonanilide | (6) |
| 37 | 2-chloro-4-nitrotrifluoromethanesulfonanilide (7) | 87–88 |
| 38 | 3-methoxytrifluoromethanesulfonanilide | 63–65 |
| 39 | 4-methoxytrifluoromethanesulfonanilide | 38–41 |
| 40 | 3-ethoxytrifluoromethanesulfonanilide | 48–48.5 |
| 41 | 4-ethoxytrifluoromethanesulfonanilide | 48–49 |
| 42 | 3-methylthiotrifluoromethanesulfonanilide | 36–37.5 |
| 43 | 4-methylthiotrifluoromethanesulfonanilide | 58–60 |
| 44 | 3-methylsulfinyltrifluoromethanesulfonanilide (8) | 115–116 |
| 45 | 4-methylsulfinyltrifluoromethanesulfonanilide (9) | 142–143 |
| 46 | 3-methylsulfonyltrifluoromethanesulfonanilide (10) | 99–100 |
| 47 | 4-methylsulfonyltrifluoromethanesulfonanilide (11) | 166–166.5 |
| 48 | 3-acetyltrifluoromethanesulfonanilide | 100–102.5 |
| 49 | 3-hydroxytrifluoromethanesulfonanilide | 98–100 |
| 50 | 3-(1-hydroxyethyl)trifluoromethanesulfonanilide (12) | (13) |
| 51 | 4-aminotrifluoromethanesulfonanilide (14) | 104.5–106 |
| 52 | 4-acetamidotrifluoromethanesulfonanilide | 152.5–154 |
| 53 | 3-acetamidotrifluoromethanesulfonanilide | 159–161 |
| 54 | 2-acetyltrifluoromethanesulfonanilide | 53.5–56.5 |
| 55 | 3-cyanotrifluoromethanesulfonanilide | 112.5–115 |
| 56 | 2,5-dibromotrifluoromethanesulfonanilide | 73.4–76 |
| 57 | 3-chloro-6-methylthiotrifluoromethanesulfonanilide | 66.5–67.5 |
| 58 | 4-propionyltrifluoromethanesulfonanilide | 141–142 |
| 59 | 2-fluoro-5-trifluoromethyltrifluoromethanesulfonanilide | 52–54 |
| 60 | 2-carbamyltrifluoromethanesulfonanilide | 156.5–158 |
| 61 | 3-trifluoromethylthiotrifluoromethanesulfonanilide | (14a) |
| 62 | 4-chloro-2-methyltrifluoromethanesulfonanilide | 89–90.5 |
| 63 | 4-chloro-2-trifluoromethyltrifluoromethanesulfonanilide | 66.5–67.5 |
| 64 | 2-isobutyroyltrifluoromethanesulfonanilide | 46–47 |
| 65 | 3-isobutyroyltrifluoromethanesulfonanilide | 90–92 |
| 66 | 2-n-butyroyltrifluoromethanesulfonanilide | (15) |
| 67 | 3-n-butyroyltrifluoromethanesulfonanilide | 82–84 |
| 68 | 3-n-hexanoyltrifluoromethanesulfonanilide | 65 |
| 69 | 2-n-hexanoyltrifluoromethanesulfonanilide | (16) |
| 70 | 4-fluoro-3-nitrotrifluoromethanesulfonanilide | 70.5–73.5 |
| 71 | 5-fluoro-2-methyltrifluoromethanesulfonanilide | 73.6–75.4 |
| 72 | 4-methyl-2-nitrotrifluoromethanesulfonanilide | 53–55 |
| 73 | 4-amino-2-methyltrifluoromethanesulfonanilide (17) | 125–126 |
| 74 | 2-iodotrifluoromethanesulfonanilide | (17a) |
| 75 | 5-chloro-2-methoxytrifluoromethanesulfonanilide | 85.4–88 |
| 76 | 2-bromo-4-fluorotrifluoromethanesulfonanilide (18) | 58–59 |
| 77 | 3-formyltrifluoromethanesulfonanilide | 103.5–105 |
| 78 | 3-bromoacetyltrifluoromethanesulfonanilide (19) | 60–62.5 |
| 79 | 3-trifluoromethylsulfonamidoacetophenone semicarbazone (20) | 180–182 |
| 80 | 2-bromo-4-methyltrifluoromethanesulfonanilide | 76–78.5 |
| 81 | 2-trifluoromethylsulfonamidophenyl-N-methylcarbamate | 85.5–87 |
| 82 | 4-chloro-2-trifluoromethylsulfonamidobenzamide | 134–135.5 |
| 83 | 2-chloro-4-fluorotrifluoromethanesulfonanilide (21) | 57–58.5 |

-continued

| Example No. | | M.P. ° C. |
|---|---|---|
| 84 | 4-chloro-2-fluorotrifluoromethanesulfonanilide (22) | (23) |
| 85 | 2-fluoro-4-methyltrifluoromethanesulfonanilide | 53.4–55.8 |
| 86 | 2-methoxy-5-nitrotrifluoromethanesulfonanilide | 109–110.5 |
| 87 | 4-hydroxytrifluoromethanesulfonanilide | 107–108 |
| 88 | 4-amino-2-trifluoromethyltrifluoromethanesulfonanilide (24) | 122.5–124 |
| 89 | 4-bromo-2-chlorotrifluoromethanesulfonanilide | 114.4–115.3 |
| 90 | 2-bromo-4-chlorotrifluoromethanesulfonanilide | 105–106 |
| 91 | 2-acetamido-4-methoxytrifluoromethanesulfonanilide (25) | 161.5–163 |
| 92 | 3-trifluoromethylsulfonamidoacetophenone oxime (26) | 126.5–127 |
| 93 | 5-acetyl-2-methoxytrifluoromethanesulfonanilide | 105.5–107.5 |
| 94 | methyl 4-trifluoromethylsulfonamidobenzoate | 150–151 |
| 95 | 4-sulfamoyltrifluoromethanesulfonanilide | 147–149 |
| 96 | 5-chloro-2-sulfamoyltrifluoromethanesulfonanilide | 189–190 |
| 97 | 2-methylthiotrifluoromethanesulfonanilide | 52.5–53 |
| 98 | 2,6-dichlorotrifluoromethanesulfonanilide | 141–142.5 |
| 99 | 2-methylsulfonyltrifluoromethanesulfonanilide (27) | 91–91.5 |
| 100 | 2,4-dimethoxytrifluoromethanesulfonanilide | 60.8–61.5 |
| 101 | 3,4,5-trichlorotrifluoromethanesulfonanilide | 110.3–111.5 |
| 102 | 2,6-dinitro-4-trifluoromethyltrifluoromethanesulfonanilide (28) | 106–107 |
| 103 | 2,5-dichloro-4-nitrotrifluoromethanesulfonanilide | 97–98.2 |
| 104 | 2-methoxytrifluoromethanesulfonanilide | 57–58 |
| 105 | 4-fluoro-2-trifluoromethyltrifluoromethanesulfonanilide | (29) |
| 106 | 4-chloro-3-sulfamoyltrifluoromethanesulfonanilide | 169–171.5 |
| 107 | 2,5-difluorotrifluoromethanesulfonanilide | 79–80 |
| 108 | 3,5-bis(trifluoromethyl)trifluoromethanesulfonanilide | (30) |
| 109 | 3-chloro-4-(dimethylamino)trifluoromethanesulfonanilide | 85–86 |
| 110 | 4-chloro-3-trifluoromethyltrifluoromethanesulfonanilide | 89–90.5 |
| 111 | 4-fluoro-2-methyltrifluoromethanesulfonanilide | 42.5–43.7 |
| 112 | 2-methoxy-4-nitrotrifluoromethanesulfonanilide | 103–105 |
| 113 | 2-methylsulfinyltrifluoromethanesulfonanilide (31) | 115.5–117.5 |
| 114 | N-(4-trifluoromethylsulfonamidophenyl)glycinamide (32) | 157–160 |
| 115 | 2,6-dichloro-4-nitrotrifluoromethanesulfonanilide | 157–159.5 |
| 116 | 2,4-bis(methylthio)trifluoromethanesulfonanilide | 87–88 |
| 117 | 5-acetamido-2-methoxytrifluoromethanesulfonanilide (32A) | 198.5–199 |
| 118 | 2,4-bis(methylsulfonyl)trifluoromethanesulfonanilide (33) | 190–191 |
| 119 | 4-chloro-3-nitrotrifluoromethanesulfonanilide | 71–72.5 |
| 120 | 3-aminotrifluoromethanesulfonanilide (34) | 104.5–106 |
| 121 | 2-amino-4-chlorotrifluoromethanesulfonanilide (35) | 117.5–118 |
| 122 | 4-amino-2,5-dichlorotrifluoromethanesulfonanilide (36) | 153–154 |
| 123 | 4-chloro-2-methylthiotrifluoromethanesulfonanilide | 62.0–62.5 |
| 124 | 4-(2,2,2-trifluoroethylthio)trifluoromethanesulfonanilide | 62–63.5 |
| 125 | 3-propionamidotrifluoromethanesulfonanilide | 130.5–132 |
| 126 | 2-hydroxytrifluoromethanesulfonanilide (37) | 83–86 |
| 127 | 2,6-dichloro-4-fluorotrifluoromethanesulfonanilide (38) | 95–96 |
| 128 | 4-trifluoromethylsulfonamidophenylacetic acid (39) | 134–137 |
| 129 | 2-methyl-5-nitrotrifluoromethanesulfonanilide | 102.5–104 |
| 130 | 2-chloro-5-nitrotrifluoromethanesulfonanilide | 97–98.5 |
| 131 | 5-amino-2-chlorotrifluoromethanesulfonanilide (40) | 88.5–90.5 |
| 132 | 3-chloro-4-fluorotrifluoromethanesulfonanilide | 70.5–72 |
| 133 | 2,4-dichloro-6-fluorotrifluoromethanesulfonanilide (41) | 63.5–64.5 |
| 134 | 3-trifluoromethylsulfonamidophenyl-N-methylcarbamate (42) | 126.5–128 |
| 135 | 2-acetamidotrifluoromethanesulfonanilide (43) | 159–160 |
| 136 | 5-amino-2-methyltrifluoromethanesulfonanilide (44) | 120–121 |
| 137 | 4-trifluoromethylsulfonamidophenyl-N-methylcarbamate (45) | 150.5–153 |
| 138 | 4-nitro-2-trifluoromethyltrifluoromethanesulfonanilide | 65–66.5 |
| 139 | 4-bromo-2-trifluoromethyltrifluoromethanesulfonanilide | 80–82 |
| 140 | 3-(n-butylthio)trifluoromethanesulfonanilide (46) | (47) |
| 141 | 2-nitro-4-trifluoromethyltrifluoromethanesulfonanilide | (48) |
| 142 | 2-methyl-4-nitrotrifluoromethanesulfonanilide | 104.5–106 |
| 143 | 2-chloro-4-trifluoromethyltrifluoromethanesulfonanilide | 91.5–92.5 |
| 144 | 2-(2,2,2-trifluoroethoxy)trifluoromethanesulfonanilide (49) | 79–81 |
| 145 | 4-(2,2,2-trifluoroethoxy)trifluoromethanesulfonanilide (49) | 86–89 |
| 146 | 2,6-dichloro-4-trifluoromethyltrifluoromethanesulfonanilide | 109–111 |
| 147 | 2-mercaptotrifluoromethanesulfonanilide | 61–63.5 |
| 148 | 4-methoxy-2-nitrotrifluoromethanesulfonanilide | 77.3–79.3 |
| 149 | 3-trifluoromethylsulfonyltrifluoromethanesulfonanilide | 104–105 |
| 150 | 3,5-dichloro-4-(2,2,2-trifluoroethoxy)trifluoromethanesulfonanilide (50) | 125–126 |
| 151 | 4-trifluoromethylsulfonamidoacetophenone oxime (51) | 117–119 |
| 152 | 4-bromo-2-fluorotrifluoromethanesulfonanilide (52) | 90.5–91.5 |
| 153 | 4-trifluoromethylsulfonyltrifluoromethanesulfonanilide | 140.5–142.5 |
| 154 | 2-chloro-3-methyltrifluoromethanesulfonanilide | 84–86 |
| 155 | 2-fluoro-5-methyltrifluoromethanesulfonanilide | 93–95.5 |
| 156 | N-(3-trifluoromethylsulfonoxy)trifluoromethanesulfonanilide (53) | (54) |
| 157 | 3-fluoro-4-methyltrifluoromethanesulfonanilide | 55.7–58.2 |
| 158 | 4-trifluoromethylthiotrifluoromethanesulfonanilide | 60.5–62 |
| 159 | 2-bromo-4-trifluoromethyltrifluoromethanesulfonanilide (55) | 78–80 |
| 160 | 2-aminotrifluoromethanesulfonanilide (55a) | 103–103.8 |
| 161 | 5-(chloroacetamido)-2-methyltrifluoromethanesulfonanilide (56) | 196–197.5 |
| 162 | ethyl N-(4-trifluoromethylsulfonamidophenyl)glycinate (57) | 125–127 |
| 163 | 4-fluoro-3-methyltrifluoromethanesulfonanilide | (58) |
| 164 | 5-acetamido-2-chlorotrifluoromethanesulfonanilide (59) | 186–188 |
| 165 | 2-chloro-5-chloroacetamidotrifluoromethanesulfonanilide (60) | 188.5–190 |
| 166 | 3-acetamido-4-chlorotrifluoromethanesulfonanilide | 186.5–188 |
| 167 | 4-methyl-3-nitrotrifluoromethanesulfonanilide | 75–76.5 |
| 168 | ethyl N-(2-chloro-5-trifluoromethylsulfonamidophenyl)carbamate (60A) | 134.5–135.5 |
| 169 | 3-amino-4-methyltrifluoromethanesulfonanilide (61) | 73–74 |
| 170 | 2-chloro-4-methyltrifluoromethanesulfonanilide | 83.5–85 |
| 171 | 3-(n-hexadecylthio)trifluoromethanesulfonanilide | 63–65 |
| 172 | 2-chloro-5-methyltrifluoromethanesulfonanilide | 86.5–88 |
| 173 | 2-amino-4-trifluoromethyltrifluoromethanesulfonanilide (62) | 123–124 |
| 174 | 2-nitro-4-trifluoromethyltrifluoromethanesulfonanilide (63) | (64) |
| 175 | ethyl (4-methyl-3-trifluoromethylsulfonamidophenyl)carbamate (65) | 142–143.5 |

-continued

| Example No. | | M.P. ° C. |
|---|---|---|
| 176 | 4-fluoro-3-trifluoromethyltrifluoromethanesulfonanilide | (66) |
| 177 | 2-cyanotrifluoromethanesulfonanilide | (65a) |
| 178 | 4-cyanotrifluoromethanesulfonanilide | 147–149 |
| 179 | 3-acetamido-4-methyltrifluoromethanesulfonanilide (67) | 140.5–142 |
| 180 | 2,5-dimethoxytrifluoromethanesulfonanilide | 63–65 |
| 181 | 3,4-diethoxytrifluoromethanesulfonanilide | 78.2–79.2 |
| 182 | 5-chloro-2,4-dimethoxytrifluoromethanesulfonanilide | 109.5–110 |
| 183 | 4-mercaptotrifluoromethanesulfonanilide | (68) |
| 184 | 3-trifluoromethyltrifluoromethanesulfonanilide | (69) |
| 185 | 2-acetamido-4-trifluoromethyltrifluoromethanesulfonanilide (70) | 193–194.5 |
| 186 | 3-chloro-4-methyltrifluoromethanesulfonanilide | 57–60 |
| 187 | 3-amino-4-chlorotrifluoromethanesulfonanilide (71) | 84.5–86 |

(1) Prepared by acetylation of 5-amino-2-methyltrifluoromethanesulfonanilide (the compound of Example 136) with acetic anhydride.
(2) boiling point 135–145° C./1 mm.
(3) Prepared by Method B
(4) Prepared by Method B
(5) Prepared by Method B
(6) A red oil. Analysis: Calculated C, 27.6; H, 1.3 Found C, 27.9; H, 1.5
(7) Prepared by Method B
(8), (9) The synthesis of the mercaptosulfonanilide by Method A was followed by oxidation with one equivalent of hydrogen peroxide in acetone.
(10), (11) The synthesis of the mercaptosulfonanilide using Method A was followed by oxidation with two equivalents of hydrogen peroxide in acetic acid.
(12) Compound 48 (3-acetyltrifluoromethanesulfonanilide) was reduced with sodium borohydride according to the method disclosed in A. I. Vogel, "Practical Organic Chemistry", p. 881, Wiley and Sons, N.Y. (1956).
(13) A colorless liquid, b.p. 174° C./0.8 mm. Analysis: Calculated C, 40.2; H, 3.8. Found: C, 40.2; H, 3.7.
(14) Compound 2 (4-nitrotrifluoromethanesulfonanilide) was catalytically reduced using 5% palladium on charcoal.
(14a) b.p. 102° C./0.45 mm.
(15) A clear liquid. Analysis: Calculated C, 44.8; H, 4.1. Found: C, 44.6; H, 4.3.
(16) A clear liquid. Analysis: Calculated C, 48.2; H, 5.0; N, 4.3 Found: C, 48.5; H, 5.0; N, 4.3.
(17) Prepared by reduction of the compound of Example 142 with Raney nickel and hydrogen.
(17a) b.p. 95° C./0.075 mm.
(18) Preferably prepared by the bromination of 4-fluorotrifluoromethanesulfonanilide in an ethanol-water solution of bromine.
(19) Prepared from compound 48 (3-acetyltrifluoromethanesulfonanilide) by bromination with cupric bromide according to L. C. King and C. K. Ostrum, J. Org. Chem. 29, 3459 (1964).
(20) This compound is prepared from compound 48 (3-acetyltrifluoromethanesulfonanilide) by the method disclosed in R. T. Shriner, et al., "Systematic Identification of Organic Compound" p. 218, Wiley, N.Y. (1956).
(21) Preferably prepared by chlorination of 4-fluorotrifluoromethanesulfonanilide in acetic acid in the presence of aluminum chloride.
(22) Preferably prepared by chlorination of 2-fluorotrifluoromethanesulfonanilide in acetic acid in the presence of aluminum chloride.
(23) Tan crystals, b.p. 75–80° C./.05 mm. Analysis: Calculated C, 30.3; H, 1.5; N, 5.1. Found C, 29.7; H, 1.4; N, 4.7.
(24) Prepared by reduction of the compound of Example 138 with Raney nickel.
(25) Prepared by reduction of the compound of Example 10 with Raney nickel and hydrogen followed by acetylation with acetic anhydride.
(26) This compound was prepared from compound 48 (3-acetyltrifluoromethanesulfonanilide) by the method disclosed in R. T. Shriner, et al., "Systematic Identification of Organic Compounds", p. 254, Wiley, N.Y. (1956).
(27) Prepared by oxidation of the compound of Example 97 (2-methylthiosulfamoyltrifluoromethanesulfonanilide) with two equivalents of hydrogen peroxide in acetic acid.
(28) Prepared by reaction of 2,6-dinitro-4-trifluoromethylchlorobenzene with trifluoromethanesulfonamide sodium salt.
(29) A liquid, b.p. 43–45° C./0.2 mm. Analysis: calculated C, 30.8; H, 1.3 Found C, 30.9; H, 1,3.
(30) A liquid, b.p. 89–91° C./0.5 mm. Analysis: calculated C, 29.7; H. 1.1 Found C, 29.8; H, 1.1.
(31) Prepared by oxidation of the compound of Example 97 (2-methylthiotrifluoromethanesulfonanilide) with one equivalent of hydrogen peroxide in acetone.
(32) Prepared by reaction of the compound of Example 162 (ethyl N-(4-trifluoromethylsulfonamidophenyl)glycinate) with ammonia.
(32A) Prepared by reduction of the compound of Example 136 with Raney nickel and hydrogen followed by acetylation with acetic anhydride.
(33) Prepared by oxidation of the compound of Example 116 (2,4-bis(methylthio)trifluoromethanesulfonanilide) with 4 equivalents of hydrogen peroxide in acetic acid.
(34) Prepared by reduction of the compound of Example 34 (3-nitrotrifluoromethanesulfonanilide) with hydrogen over 5% palladium on charcoal.
(35) Prepared by reduction of the compound of Example 36 (4-chloro-2-nitrotrifluoromethanesulfonanilide) with hydrogen over 5% palladium on charcoal.
(36) Prepared by reduction of the compound of Example 103 (2,5-dichloro-4-nitrotrifluoromethanesulfonanilide) with hydrogen over 5% palladium on charcoal.
(37) prepared by reaction of the compound of Example 104 (2-methoxytrifluoromethanesulfonanilide) with hydroiodic acid in acetic acid.
(38) Prepared by chlorination of the compound of Example 7 (4-fluorotrifluoromethanesulfonanilide) at 100° C. in glacial acetic acid.
(39) Prepared by basic hydrolysis of methyl 4-trifluoromethylsulfonamidophenylacetate.
(40) Prepared by reduction of the compound of Example 130 (2-chloro-5-nitrotrifluoromethanesulfonanilide).
(41) Prepared by chlorination of the compound of Example 5 (2-fluorotrifluoromethanesulfonanilide) in acetic acid with aluminum chloride as catalyst.
(42) Prepared by reaction of the compound of Example 49 (3-hydroxytrifluoromethanesulfonanilide) with methyl isocyanate.
(43) Prepared by reduction of the compound of Example 33 (2-nitrotrifluoromethanesulfonanilide) followed by acetylation.
(44) Prepared by reduction of the compound of Example 129 (2-methyl-5-nitrotrifluoromethanesulfonanilide) with hydrogen and Raney nickel.
(45) Prepared by reaction of the compound of Example 87 (4-hydroxytrifluoromethanesulfonanilide) with methyl isocyanate.
(46) Prepared by reaction of the compound of Example 15 (3-bromotrifluoromethanesulfonanilide) with the copper salt of n-butanethiol.
(47) A yellow liquid, b.p. 136° C./0.01 mm. Analysis: Calculated C, 42.4; H, 4.5 Found C, 42.5; H, 4.5.
(48) b.p. 105° C./3.5 mm.
(49) These compounds are prepared by the usual process (method A). The anilines are obtained by reacting the known aminophenols with sodium hydride to form the phenolate salts, and reacting these salts with 2,2,2-trifluoroethyl trifluoromethanesulfonate.
(50) This compound is prepared by the usual process (Method A). The anilines are obtained by reacting the known aminophenols with sodium hydride to form the phenolate salts, and reacting these salts with 2,2,2-trifluoroethyl trifluoromethanesulfonate.
(51) This compound is prepared by the compound of Example 1 (4-acetyltrifluoromethanesulfonanilide) by the method disclosed in R. T. Shriner et al., "Systematic Identification of Organic Compounds", p. 254, Wiley, N.Y. (1956).
(52) This compound is prepared from the compound of Example 5 (2-fluorotrifluoromethanesulfonanilide) by bromination in ethanol-water.
(53) This compound is prepared from the compound of Example 49 (3-hydroxytrifluoromethanesulfonanilide) by reaction with trifluoromethanesulfonyl chloride.
(54) A colorless oil, b.p. 110° C./0.1 mm. Analysis: Calculated C, 25.7; H, 1.4; N, 3.8. Found: C, 25.9; H, 1.4; N, 3.9.
(55) This compound is prepared from the compound of Example 19 (4-trifluoromethyltrifluoromethanesulfonanilide) by bromination in ethanol-water.
(55a) Prepared by reduction of the compound of Example 33 with Raney nickel and hydrogen.
(56) This compound is prepared by the reaction of the compound of Example 136 (5-amino-2-methyltrifluoromethanesulfonanilide) with chloroacetyl chloride.
(57) This compound is prepared by the reaction of the compound of Example 51 (4-aminotrifluoromethanesulfonanilide) with ethyl bromoacetate.

-continued

(58) b.p. 85° C./0.15 mm.
(59) This compound is prepared by the reaction of the compound of Example 131 (5-amino-2-chlorotrifluoromethanesulfonanilide).
(60) This compound is prepared by the reaction of the compound of Example 131 (5-amino-2-chlorotrifluoromethanesulfonanilide) with chloroacetyl chloride.
(60A) This compound is prepared by the reaction of the compound of Example 187 (3-amino-4-chlorotrifluoromethanesulfonanilide) with ethyl chloroformate.
(61) This compound is prepared by reduction of the corresponding nitro compound which is prepared by Method A.
(62) This compound is prepared by reduction of the corresponding compound of Example 174 (2-nitro-4-trifluoromethyltrifluoromethanesulfonanilide).
(63) This compound is prepared by nitration of the compound of Example 19 (4-trifluoromethyltrifluoromethanesulfonanilide).
(64) A light yellow oil, b.p. 88° C./0.2 mm. Analysis: Calculated C, 28.4; H, 1.2; N, 8.3 Found: C, 28.6; H, 1.2; N 8.3.
(65) This compound is prepared by reaction of the compound of Example 136 (5-amino-2-methyltrifluoromethanesulfonanilide) with ethyl chloroformate.
(65a) b.p. 105° C./0.1 mm.
(66) b.p. 114° C./0.6 mm.
(67) This compound is prepared by reaction of the compound of Example 169 (3-amino-4-methyltrifluoromethanesulfonanilide) with acetic anydride.
(68) Yellow crystals, b.p. 140° C./0.23 mm. Analysis: Calculated C, 32.7; H, 2.4; N, 5.5. Found C, 33.0; H, 2.4; N, 5.5.
(69) Clear liquid, b.p. 57° C./0.13 mm. Analysis: Calculated C, 32.8; H, 1.7 Found C, 33.0; H, 1.7.
(70) Prepared by reaction of the compound of Example 173 (2-amino-4-trifluoromethyltrifluoromethanesulfonanilide) with acetyl chloride in the presence of triethylamine in benzene.
(71) Prepared by reduction of the compound of Example 119 (4-chloro-3-nitrotrifluoromethanesulfonanilide) with Raney nickel and hydrogen.

Certain salts of the invention are prepared and described in the following examples. In examples 188 through 193, 2,4-dichlorotrifluoromethanesulfonanilide (Example 3) was reacted with the appropriate amine in an inert organic solvent (for example diethyl ether, benzene or chloroform). Evaporation of the volatile portion of the reaction mixture gave the dry salt which was purified by recrystallization.

| Example No. | | M.P. ° C. |
| --- | --- | --- |
| 188 | isopropylammonium-2,4-dichlorotrifluoromethanesulfonanilide | 145–146 |
| 189 | triethylammonium-2,4-dichlorotrifluoromethanesulfonanilide | 120–121.5 |
| 190 | methylammonium-2,4-dichlorotrifluoromethanesulfonanilide | 146–148 |
| 191 | dimethylammonium-2,4-dichlorotrifluoromethanesulfonanilide | 80.5–83.5 |
| 192 | di-n-decylammonium-2,4-dichlorotrifluoromethanesulfonanilide | 43.5–45 |
| 193 | 2-methyl-2-pseudothiouronium 2,4-dichlorotrifluoromethanesulfonanilide | 96–97.5 |

EXAMPLE 194

2,4-Dichlorotrifluoromethanesulfonanilide (Example 3) was reacted with aqueous sodium hydroxide. Water was removed and the salt, sodium 2,4-dichlorotrifluoromethanesulfonanilide, purified by recrystallization from benzene/hexane. The product was recovered in the form of white flakes melting at 196.5°–197.5° C. The analytical results ($C_7H_3Cl_2F_3NaNO_2S$) were as follows: Calc: C, 26.6; H, 1.0 Found: C, 26.6; H, 1.2.

EXAMPLE 195

2,4-Dichlorotrifluoromethanesulfonanilide was heated with barium hydride in dimethoxyethane, then the solvent was removed and the barium salt recrystallized from dimethoxyethane/hexane. The product was recovered as a white solid melting above 300° C. The analytical results ($C_{14}H_8BaCl_4F_6N_2O_4S_2$) were as follows: Calc: C, 23.3; H, 0.8 Found: C, 23.5; H, 1.0.

EXAMPLE 196

2,4-Dichlorotrifluoromethanesulfonanilide was heated with calcium hydride in dimethoxyethane, then the solvent was removed and the calcium salt was recrystallized from dimethoxyethane/hexane. The product was recovered as a white hygroscopic solid melting above 275° C. The analytical results ($C_{14}H_6CaCl_4F_6N_2O_4S_2$) were as follows: Calc. C, 26.9; H, 1.0 Found: C, 26.9; H, 1.3.

EXAMPLE 197

5-Acetamido-2-methyltrifluoromethanesulfonanilide (Example 12) was reacted with sodium methoxide under reflux for six hours. The product was obtained by removal of the solvent in vacuo, then recrystallized from methanol/hexane. The product, sodium 5-acetamido-2-methyltrifluoromethanesulfonanilide, was recovered as colorless crystals melting above 300° C. The analytical results ($C_{10}H_{10}F_3N_2NaO_3S$) were as follows: Calc.: C, 37.7; H, 3.2; N, 8.8 Found: C, 37.8; H, 3.5; N, 9.0.

EXAMPLE 198

5-acetamido-2-methyltrifluoromethanesulfonanilide (1 equivalent) is reacted with diethanolamine (1 equivalent) to give diethanolammonium 5-acetamido-2-methyltrifluoromethanesulfonanilide.

EXAMPLE 199

The compound of Example 199 was prepared by reacting the compound of Example 1 with an equimolar amount of aqueous sodium bicarbonate and removing the water to form the pure salt, sodium 4-acetyltrifluoromethanesulfonanilide as a white powder melting at 275° C.

Analysis: Calculated for $C_9H_7F_3NaNO_3S$: C, 37.4; H, 2.44 Found: C, 37.2; H, 2.6.

EXAMPLE 200

The compound of Example 48 was reacted with an equimolar amount of aqueous sodium bicarbonate and water was removed to form pure 3-acetyltrifluoromethanesulfonanilide as a white solid.

Analysis: Calculated for $C_9H_7F_3NaNO_3S$: C, 37.4; H, 2.44 Found: C, 37.4; H, 2.4.

Compounds in which the perfluoroalkyl group is varied are shown in the following examples which are presented in table form. Unless otherwise specified, the compounds set out in the table have been prepared using Method A from known starting materials. The melting points are uncorrected.

| Ex. No. | | M.P. ° C. |
|---|---|---|
| 201 | 4-chloroperfluoro-n-butanesulfonanilide | 76–78 |
| 202 | 2,4-difluoroperfluoroisopropanesulfonanilide | 67.5–68.5 |
| 203 | 4-methylthioperfluoro-n-butanesulfonanilide | 89–90.5 |
| 204 | 2,4-difluoroperfluoro-n-butanesulfonanilide | 39.5–40.5 |
| 205 | 2,4-difluoroperfluoroethanesulfonanilide | 33–35 |
| 206 | 4-methylsulfinylperfluoroethanesulfonanilide[72] | 162–163.5 |
| 207 | 4-trifluoromethylperfluoroethanesulfonanilide | 75–77 |
| 208 | 4-methylsulfonylperfluoroethanesulfonanilide[73] | 122–123 |
| 209 | 2,4-dichloroperfluoroethanesulfonanilide | 51–52 |
| 210 | 4-methylthioperfluoroethanesulfonanilide | (74) |

[72]Prepared by oxidation of the compound of Example 210 with hydrogen peroxide (1 equivalent) in acetone.
[73]Prepared by oxidation of the compound of Example 210 with hydrogen peroxide (2 equivalents) in acetic acid.
[74]A colorless liquid, b.p. 114° C./50 microns. Analysis:
Calculated C, 33.6; H, 2.5; N, 4.4
Found    C, 33.5; H, 2.7; N, 4.3.

EXAMPLE 211

(Method C)

Trifluoromethanesulfonamide (14.9 g., 0.10 mole), potassium hydroxide (5.6 g., 0.10 mole) and ethanol (90 ml.) were heated one hour at 50° C. This reaction mixture was evaporated to dryness in vacuo. A solution of 2,4-dinitrofluorobenzene (18.6 g., 0.10 mole) in dimethylsulfoxide (80 ml.) was added, the mixture was stirred at about 60° C. for 1 day, water was added and the mixture was refrigerated. The solid product, sodium 2,4-dinitrotrifluoromethanesulfonanilide hydrate was recrystallized from ethanol, m.p. 188°–192° C.

Analysis: Calculated for $C_7H_5F_3NaN_3O_7S$; C, 23.7; H, 1.4; N, 11.8 Found: C, 23.0; H, 1.1; N, 11.0.

The following table includes a number of additional compounds of the invention which have also been prepared by Method A except as otherwise noted.

| Example No. | | M.P. ° C. |
|---|---|---|
| 212 | 2-methyl-5-propionamidotrifluoromethanesulfonanilide[75] | 180.5–182 |
| 213 | 4-acetamido-2-methyltrifluoromethanesulfonanilide[76] | 158.5–160 |

[75]Prepared by reaction of the compound of Example 136 with propionyl chloride.
[76]Prepared by acetylation of the compound of Example 73 with acetic anhydride.

| Ex. No. | |
|---|---|
| 231 | 3-ethylsulfinyltrifluoromethanesulfonanilide, m.p. 118–120 |
| 232 | 3-ethylsulfonyltrifluoromethanesulfonanilide, m.p. 68–71 |
| 233 | 3-n-propylsulfonyltrifluoromethanesulfonanilide, m.p. 106–110 |
| 234 | 4-ethylsulfonyltrifluoromethanesulfonanilide, m.p. 135–137 |

HERBICIDAL ACTIVITY

The herbicidal activity of a number of the compounds is exemplified in the following Examples. Both pre- and post-emergence activity were determined in a direct screen against selected weed species. For the pre-emergence test, the following weed mixtures were planted in four rows in 6-inch plastic pots.

Grasses

Giant Foxtail (*Setaria faberii*)
Barnyard grass (*Echinochloa crusgalli*)
Crabgrass (*Digitaria ischaemum*)
Quackgrass (*Agropyron repens*)

Broadleaves

Pigweed (*Amaranthus retroflexus*)
Purslane (*Portulaca oleracea*)
Wild Mustard (*Brassica kaber*)
Wild Morning Glory (*Convolvulus arvensis*)

Two species were planted per row to allow for easier identification of the grass species as they emerge. 250 mg. of the test chemical was dissolved in acetone or another suitable solvent and then diluted with 125 ml. water to give a concentration of 2000 ppm. From this concentration, 60 ml. was diluted to 240 ml. to give a final concentration of 500 ppm. Eighty ml. of this solution was added to a 6 inch pot to give a concentration equivalent to 20 lbs./acre. All subsequent waterings were made from the bottom. Two pots were used per treatment. Data were taken two to three weeks after treatment and recorded as percent kill for each species compared to the untreated controls.

| Example No. | |
|---|---|
| 214 | 5-chloro-2-methyltrifluoromethanesulfonanilide, m.p. 86–88 |
| 215 | 3-ethylthiotrifluoromethanesulfonanilide, b.p. 108–110/0.08 mm., m.p. 42.5–46 |
| 216 | 4-ethylthiotrifluoromethanesulfonanilide, m.p. 32–34 |
| 217 | 3-isopropylthiotrifluoromethanesulfonanilide, b.p. 120–124/0.2 mm. |
| 218 | 3-chloro-2-methyltrifluoromethanesulfonanilide, m.p. 116–118 |
| 219 | 2-bromo-4-methylsulfonyltrifluoromethanesulfonanilide, m.p. 143–145 |
| 220 | 4-N,N-dimethylsulfamoyltrifluoromethanesulfonanilide, m.p. 174–176 |
| 221 | 4-(N,N-dimethylsulfamoyl)-2-methyltrifluoromethanesulfonanilide, m.p. 163–165 |
| 222 | 2-methyl-4-(N-methylsulfamoyl)trifluoromethanesulfonanilide, m.p. 135–138 |
| 223 | 3-(N,N-dimethylsulfamoyl)trifluoromethanesulfonanilide, m.p. 105–108 |
| 224 | 3-(N-methylsulfamoyl)trifluoromethanesulfanilide, m.p. 98–100 |
| 225 | 5-(N,N-dimethylsulfamoyl)-2-methyltrifluoromethanesulfonanilide, m.p. 150–160 |
| 226 | 3-n-propylthiotrifluoromethanesulfonanilide, b.p. 115–121/5 mm. |
| 227 | 2-(N-methylcarbamyl)trifluoromethanesulfonanilide, m.p. 91–96 |
| 228 | 2-(N,N-diethylcarbamyl)trifluoromethanesulfonanilide, m.p. 116–119 |
| 229 | 3-(methoxymethylthio)trifluoromethanesulfonanilide, b.p. 140° C./5 mm. |
| 230 | 3-(N,N-dimethylsulfamoylamino)trifluoromethanesulfonanilide, m.p. 129–133 |

In order to assess post-emergence activity, the same weed mixture as described above was used. The mixture was planted in 5 × 5 inch boxes and allowed to grow from 2 to 3 weeks depending on the time of the year. The plants were treated when the grasses were approximately 1 to 3 inches and the broadleaves 1-½ inches tall. Duplicate boxes were sprayed one at a time with a concentrate sprayer (DeVilbis') for approximately 10 seconds or until good wetting of the leaf surfaces occurred. The chemicals were prepared as described above but utilizing only the 2000 ppm. concentration. Data were taken two to three weeks after treatment and recorded as percent kill for each species compared to the untreated controls. Results are presented in the following tables as an average of the activity observed for the 4 grasses and for 4 broadleaves in the pre- and post-emergence tests.

| Compound Designation | Grasses, % Kill Pre-emergence | Grasses, % Kill Post-emergence | Broadleaf, % Kill Pre-emergence | Broadleaf, % Kill Post-emergence |
|---|---|---|---|---|
| 2 | 100 | 0 | 90 | 12 |
| 3 | 100 | 6 | 100 | 75 |
| 3 ** | 95 | | 98 | |
| 5 | 95 | 0 | 0 | 50 |
| 7 | 100 | 0 | 100 | 100 |
| 8 | 30 | 0 | 100 | 75 |
| 9 * | 100 | 0 | 100 | 100 |
| 10 | 100 | 0 | 100 | 100 |
| 11 | 100 | 52 | 100 | 100 |
| 11 ** | 92 | | 100 | |
| 13 * | 60 | 30 | 100 | 100 |
| 14 | 100 | 0 | 100 | 100 |
| 15 | 62 | 0 | 100 | 80 |
| 16 | 0 | 0 | 100 | 100 |
| 17 | 98 | 75 | 100 | 100 |
| 18 * | 0 | 0 | 100 | 98 |
| 19 | 97 | 0 | 100 | 92 |
| 20 * | 50 | 0 | 100 | 98 |
| 21 * | 20 | 0 | 95 | 87 |
| 22 * | 90 | 0 | 100 | 100 |
| 23 | 50 | 47 | 100 | 100 |
| 24 | 100 | 0 | 100 | 100 |
| 25 | 92 | 50 | 82 | 90 |
| 26 | 100 | 50 | 100 | 95 |
| 27 | 50 | 0 | 75 | 100 |
| 28 | 87 | 0 | 90 | 0 |
| 29 | 90 | 0 | 100 | 100 |
| 33 | 40 | 0 | 74 | 12 |
| 34 | 0 | 0 | 72 | 25 |
| 35 | 0 | 0 | 75 | 50 |
| 37 | 0 | 25 | 50 | 100 |
| 38 | 0 | 0 | 87 | 44 |
| 39 | 95 | 0 | 100 | 0 |
| 40 | 50 | 0 | 100 | 60 |
| 41 | 50 | 0 | 100 | 45 |
| 42 | 95 | 90 | 23 | 100 |
| 43 | 100 | 20 | 100 | 74 |
| 44 | 100 | 50 | 100 | 63 |
| 46 | 100 | 25 | 100 | 38 |
| 47 | 100 | 0 | 70 | 30 |
| 52 | 62 | 0 | 72 | 0 |
| 62 | 100 | 0 | 100 | 12 |
| 188 * | 100 | | 100 | |
| 189 * | 100 | | 98 | |
| 190 * | 100 | | 100 | |
| 191 * | 100 | | 100 | |
| 194 * | 100 | | 100 | |
| 194 ** | 90 | | 95 | |
| 180 | 25 | 0 | 88 | 0 |
| 181 | 10 | 0 | 50 | 0 |
| 182 | 0 | 0 | 35 | 0 |

\* ½ rate of treatment
\*\* ¼ rate of treatment

The preferred plant growth regulating compounds of the invention show interesting and useful effects in one or more species of plants. The compound 5-acetamido-2-methyltrifluoromethanesulfonanilide is a preferred compound for the treatment of turf species. Said compound is formulated as the diethanolamine salt, 2 pounds per gallon of water in solution. The formulation should be applied on turf at rates of 1.0 to 2.0 gallons per acre in 40 to 80 gallons of water. Both warm and cool season species have responded with good vegetative growth inhibition and seedhead suppression. Vegetative inhibition lasting more than six weeks has resulted from a single application. Slight discoloration of short duration may be evident at recommended rates. Uniformity of growth suppression is dependent on thoroughness of coverage, therefore, the use of a sprayer which gives an even spray pattern and which can be accurately calibrated is desirable.

Grasses which have responded favorably include the following:
bahiagrass, *Paspalum notatum Flugge.*
bentgrass, *Agrostis palustris Huds.*
bermudagrass, *Cynodon dactylon (L.) Pers.*
bluegrass, *Poa pratensis L., P. annua L.*
dallisgrass, *Paspalum dilatatum Poir.*
fescue, *Festuca rubra L. F. arundinacea Schreb.*
orchardgrass, *Dactylis glomerata L.*
quackgrass, *Agropyron repens (L.) Beauv.*
ryegrass, *Lolium perenne L.*
St. Augustinegrass, *Stenotaphrum secundatum (Walt.) Kuntze*
zoysiagrass, *Zoysia sp. Willd.*

St. Augustinegrass, several cultivars of bluegrass, and tall fescue have responded best to the compounds with excellent top growth inhibition and seedhead suppression. Bentgrass and some cultivars of ryegrass have been injured with the compound.

The compound has induced marked growth and flower inhibition of white clover and alfalfa. Dandelion flower and seedhead formation has been significantly reduced. Dichondra has shown tolerance to the compound.

Using 5-acetamido-2-methyltrifluoromethanesulfonanilide, foliar sprays and soil drenches on tree species and woody ornamentals have given growth suppression of privet, boxwood, Monterey pine, oleander, cotoneaster, sycamore and ash. Concentration of 500 to 5000 parts per million (based on the free acid (non-salt) form of the compound) are applied during periods of rapid growth.

The treatment of soybeans and sugar cane with 5-acetamido-2-methyltrifluoromethanesulfonanilide has been found to increase yield in these crops.

In a series of tests carried out in Hawaii, the compound 5-acetamido-2-methyltrifluoromethanesulfonanilide formulated as the diethanolamine salt, 2 pounds per gallon of water, was applied to mature sugar cane up to eight weeks before harvest.

The compound provided yield increases of up to 50% of crude sugar in screening tests.

When applied aerially at rates of 2, 4 and 6 pounds of active ingredient per acre using 5 to 10 gallons of aqueous solution per acre, consistent increases in yield were obtained. These increases in yield generally were maximized when the cane was harvested at least 8 weeks after treatment.

The use of preferred compounds of the invention as herbicides, i.e. plant growth terminators, for various weed species has been carried out experimentally in the field using several types of formulations. Two types of formulations have been found to be particularly useful alternatives depending on the needs of the user and equipment available to the user of the herbicide.

The most broadly utilized formulation is a wettable powder, generally 25% or 50% by weight of the active ingredient. The inert diluent most commonly used has been a kaolin clay. About 1% of a wetting agent such as a lignosulfonate is used. These lignosulfonates are available as byproducts of the paper pulp industry and are well-known to those skilled in the art. The formulations are applied to the soil surface, generally at planting as preemergence herbicides. A well-agitated mixture of about 40 to 50 gallons of water and wettable powder combined is applied at rates of about 0.5 to 10 pounds of active ingredient per acre.

Another preferred formulation is an emulsifiable concentrate. A mixture of 2 or 4 pounds of active ingredient per gallon of, for example, xylene is prepared. About 1% of an emulsifying agent is generally used. Application of a well-agitated emulsion of 40 to 50 gallons of water and concentrate combined per acre is applied at rates of about 0.5 to 10 pounds of active ingredient per acre. The formulations are applied as preemergence herbicides to the soil surface at planting.

Crops which have been successfully treated with one or more herbicides of the invention include cotton, peanuts, soybeans, corn and grain sorghum. Successfully treated means good weed control is achieved without significant injury to the crop.

Heavy soils with slower drainage and high organic content require less active ingredient.

All of the compounds exemplified and for which physical constants have been provided herein of the present invention have been tested at various rates as herbicides and/or plant growth regulators. A variety of weed species and crops, many of which are specifically mentioned herein have been used to detect herbicidal and/or plant growth regulating activity. All of the compounds of the invention are active at rates ranging from 0.1 to 40 pounds per acre against one or more indicator species.

Included among the presently preferred herbicidal compounds of the invention are the compounds of Examples 214 through 234. These compounds have shown particularly interesting activity as herbicides in greenhouse testing, and some have also been tested in the field and found to be active.

Compounds containing the sulfamoyl group, such as N-loweralkylsulfamoyl and N,N-diloweralkylsulfamoyl are presently among the preferred compounds of the invention.

Compounds containing the sulfamoylamino group, such as N,N-diloweralkylsulfamoylamino are presently preferred compounds of the invention.

Compounds containing the alkoxyalkylthio group, particularly lower alkoxy lower alkylthio are presently preferred compounds of the invention.

What is claimed is:

1. The method for terminating the life cycle of plants which comprises contacting said plants with an effective amount of a compound of the formula:

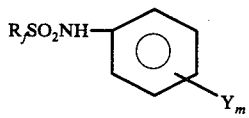

or a metal, ammonium, alkyl amine or dialkanol amine salt thereof wherein $R_f$ is a perfluoroalkyl group containing one to four carbon atoms, each Y is a non-cyclic group selected from alkyl, alkanoylamido, halo, haloalkyl, nitro, alkoxy, alkylsulfonyl, alkylsulfinyl, alkylthio, amino, sulfamoyl, carbamyl, alkoxyalkylthio and sulfamoylamino and $m$ is 1–3, provided that all of the Y groups together contain not more than about twenty carbon atoms, at least one of the Y groups contains a heteroatom selected from oxygen, sulfur, nitrogen and halogen, no single Y contains more than six carbon atoms and at least one Y is other than alkyl, halo and haloalkyl.

2. The method of claim 1 in which $R_f$ is $CF_3$.
3. The method of claim 1 in which at least one Y group is alkyl.
4. The method of claim 3 in which $R_f$ is $CF_3$.
5. The method of claim 4 in which the compound is 5-acetamido-2-methyltrifluoromethanesulfonanilide, or a salt thereof.
6. The method of claim 1 in which at least one Y group is alkanoylamido.
7. The method of claim 6 in which $R_f$ is $CF_3$.
8. The method of claim 1 in which at least one Y group is halo.
9. The method of claim 8 in which $R_f$ is $CF_3$.
10. The method of claim 1 in which at least one Y group is haloalkyl.
11. The method of claim 10 in which $R_f$ is $CF_3$.
12. The method of claim 1 in which at least one Y group is alkylsulfonyl.
13. The method of claim 12 in which $R_f$ is $CF_3$.
14. The method of claim 13 in which the compound is 3-methylsulfonyltrifluoromethanesulfonanilide, or a salt thereof.
15. The method of claim 13 in which the compound is 4-methylsulfonyltrifluoromethanesulfonanilide, or a salt thereof.
16. The method of claim 13 in which the compound is 3-ethylsulfonyltrifluoromethanesulfonanilide, or a salt thereof.
17. The method of claim 13 in which the compound is 2-bromo-4-methylsulfonyltrifluoromethanesulfonanilide or a salt thereof.
18. The method of claim 1 in which at least one Y group is alkylsulfinyl.
19. The method of claim 18 in which $R_f$ is $CF_3$.
20. The method of claim 19 in which the compound is 3-methylsulfinyltrifluoromethanesulfonanilide, or a salt thereof.
21. The method of claim 19 in which the compound is 4-methylsulfinyltrifluoromethanesulfonanilide, or a salt thereof.
22. The method of claim 19 in which the compound is 3-ethylsulfinyltrifluoromethanesulfonanilide, or a salt thereof.
23. The method of claim 1 in which at least one Y group is alkylthio.
24. The method of claim 23 in which $R_f$ is $CF_3$.
25. The method of claim 24 in which the compound is 3-methylthiotrifluoromethanesulfonanilide, or a salt thereof.
26. The method of claim 24 in which the compound is 4-methylthiotrifluoromethanesulfonanilide, or a salt thereof.
27. The method of claim 24 in which the compound is 3-ethylthiotrifluoromethanesulfonanilide, or a salt thereof.
28. The method of claim 24 in which the compound is 3-n-propylthiotrifluoromethanesulfonanilide, or a salt thereof.
29. The method of claim 1 in which at least one Y group is carbamyl.
30. The method of claim 29 in which $R_f$ is $CF_3$.

31. The method of claim 30 in which the compound is 2-carbamyltrifluoromethanesulfonanilide, or a salt thereof.

32. The method of claim 1 in which at least one Y group is sulfamoyl.

33. The method of claim 32 in which $R_f$ is $CF_3$.

34. The method of claim 33 in which the sulfamoyl group is N-alkylsulfamoyl.

35. The method of claim 34 in which the compound is 2-methyl-4-(N-methylsulfamoyl)trifluoromethanesulfonanilide, or a salt thereof.

36. The method of claim 34 in which the compound is 3-(N-methylsulfamoyl)trifluoromethanesulfonanilide, or a salt thereof.

37. The method of claim 33 in which the sulfamoyl group is N,N-diloweralkylsulfamoyl.

38. The method of claim 37 in which the compound is 4-(N,N-dimethylsulfamoyl)-2-methyltrifluoromethanesulfonanilide, or a salt thereof.

39. The method of claim 37 in which the compound is 3-(N,N-dimethylsulfamoyl)trifluoromethanesulfonanilide, or a salt thereof.

40. The method of claim 37 in which the compound is 5-(N,N-dimethylsulfamoyl)-2-methyltrifluoromethanesulfonanilide, or a salt thereof.

41. The method of claim 1 in which at least one Y group is lower alkoxyloweralkylthio.

42. The method of claim 41 in which $R_f$ is $CF_3$.

43. The method of claim 42 in which the compound is 3-(methoxymethylthio)trifluoromethanesulfonanilide, or a salt thereof.

44. The method of claim 1 in which at least one Y group is sulfamoylamino.

45. The method of claim 44 in which $R_f$ is $CF_3$.

46. The method of claim 45 in which the sulfamoylamino group is N,N-diloweralkylsulfamoylamino.

47. The method of claim 46 in which the compound is 3-(N,N-dimethylsulfamoylamino)trifluoromethanesulfonanilide, or a salt thereof.

48. A composition for terminating the life cycle of plants which comprises one or more compounds of the formula

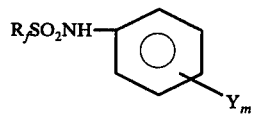

or a metal, ammonium, alkyl amine or dialkanol amine salt thereof wherein $R_f$ is a perfluoroalkyl group containing one to four carbon atoms, each Y is a non-cyclic group selected from alkyl, alkanoylamido, halo, haloalkyl, nitro, alkoxy, alkylsulfonyl, alkylsulfinyl, alkylthio, amino, sulfamoyl, carbamyl, alkoxyalkylthio and sulfamoylamino and m is 1–3, provided that all of the Y groups together contain not more than about twenty carbon atoms, at least one of the Y groups contains a heteroatom selected from oxygen, sulfur, nitrogen and halogen, no single Y contains more than six carbon atoms and at least one Y is other than alkyl, halo and haloalkyl, together with a horticulturally acceptable extending medium.

* * * * *

UNITED STATES PATENT AND TRADEMARK OFFICE
CERTIFICATE OF CORRECTION

PATENT NO. : 4,076,519

DATED : February 28, 1978

INVENTOR(S) : Joseph Kenneth Harrington, Donald C. Kvam, Arthur Mendel and Jerry E. Robertson It is certified that error appears in the above-identified patent and that said Letters Patent are hereby corrected as shown below:

Column 17, Example 224, "trifluoromethanesulfanilide" should read --trifluoromethanesulfonanilide-- .

Column 18, before Example 231, insert:

--The following compounds are prepared by oxidation of the corresponding alkylthio compounds with hydrogen peroxide in acetic acid. One equivalent of hydrogen peroxide was used for Example 231 and two equivalents for Examples 232, 233 and 234.--

Signed and Sealed this

Third Day of October 1978

[SEAL]

Attest:

RUTH C. MASON
Attesting Officer

DONALD W. BANNER
Commissioner of Patents and Trademarks